(12) United States Patent
Akura

(10) Patent No.: US 11,547,553 B2
(45) Date of Patent: Jan. 10, 2023

(54) ACCOMMODATIVE INTRAOCULAR LENS

(71) Applicant: MIRAI EYE INC., Hyogo (JP)

(72) Inventor: Junsuke Akura, Hyogo (JP)

(73) Assignee: MIRAI EYE INC., Hyogo (JP)

( * ) Notice: Subject to any disclaimer, the term of this patent is extended or adjusted under 35 U.S.C. 154(b) by 91 days.

(21) Appl. No.: 16/640,816

(22) PCT Filed: Oct. 2, 2018

(86) PCT No.: PCT/JP2018/036940
§ 371 (c)(1),
(2) Date: Feb. 21, 2020

(87) PCT Pub. No.: WO2019/069948
PCT Pub. Date: Apr. 11, 2019

(65) Prior Publication Data
US 2020/0276011 A1    Sep. 3, 2020

(30) Foreign Application Priority Data

Oct. 3, 2017    (JP) .............................. JP2017-193278

(51) Int. Cl.
*A61F 2/16* (2006.01)

(52) U.S. Cl.
CPC ........ *A61F 2/1605* (2015.04); *A61F 2/16015* (2015.04); *A61F 2/1624* (2013.01)

(58) Field of Classification Search
CPC ... A61F 2/1605; A61F 2/16015; A61F 2/1624
See application file for complete search history.

(56) References Cited

U.S. PATENT DOCUMENTS 6,846,326 B2    1/2005  Zadno-Azizi
9,925,039 B2 *  3/2018  Sohn ................... A61F 2/1629
(Continued)

FOREIGN PATENT DOCUMENTS

JP    2004-523316 A    8/2004
JP    2014-140626 A    8/2014
(Continued)

OTHER PUBLICATIONS

English Translation of International Search Report for PCT/JP2018/036940 dated Jan. 15, 2019.

*Primary Examiner* — Jerrah Edwards
*Assistant Examiner* — Aren Patel
(74) *Attorney, Agent, or Firm* — Millen, White, Zelano & Branigan, P.C.; William Nixon; Wan-Ching Montfort

(57) ABSTRACT

An accommodative intraocular lens capable of effectively exerting a focus adjustment function includes an optical portion and a plurality of support portions arranged around the optical portion. The support portion includes an anterior support portion and a posterior support portion, and the anterior support portion presses an anterior capsule and the posterior support portion presses a posterior capsule by the elastic force of the support portion. When the lens capsule is in a distance vision state or in a near vision state, as the pressing force of the anterior capsule against the anterior support portion increases or decreases, the anterior support portion deflects backward or returns forward while maintaining the radial position of the base end portion, so that the tip end portion of the anterior support portion moves backward or forward greatly while maintaining the radial position, and the optical portion moves backward or forward accordingly.

19 Claims, 13 Drawing Sheets

(56) References Cited

U.S. PATENT DOCUMENTS

| | | |
|---|---|---|
| 10,052,197 B2 | 8/2018 | Dolla et al. |
| 2002/0107568 A1* | 8/2002 | Zadno-Azizi ......... A61F 2/1613 |
| | | 623/6.37 |
| 2002/0116058 A1 | 8/2002 | Zadno-Azizi |
| 2003/0065387 A1* | 4/2003 | Callahan ............... A61F 2/1613 |
| | | 623/6.25 |
| 2003/0078658 A1* | 4/2003 | Zadno-Azizi ........ B29D 11/026 |
| | | 623/6.37 |
| 2004/0111152 A1* | 6/2004 | Kelman ................ A61F 2/1629 |
| | | 623/6.37 |
| 2007/0005136 A1* | 1/2007 | Richardson ........... A61F 2/1629 |
| | | 623/6.37 |
| 2007/0100444 A1* | 5/2007 | Brady ................... A61F 2/1635 |
| | | 623/6.37 |
| 2007/0260310 A1 | 11/2007 | Richardson |
| 2012/0078364 A1* | 3/2012 | Stenger ................. A61F 2/1629 |
| | | 623/6.39 |
| 2015/0142108 A1 | 5/2015 | Akura et al. |
| 2015/0289970 A1 | 10/2015 | Akura et al. |
| 2016/0157996 A1 | 6/2016 | Dolla et al. |
| 2018/0271646 A1* | 9/2018 | Marcos Celestino ........................ A61F 2/1624 |
| 2020/0008931 A1* | 1/2020 | Argento ................ A61F 2/1635 |

FOREIGN PATENT DOCUMENTS

| | | |
|---|---|---|
| WO | 2014185136 A1 | 11/2014 |
| WO | 2016093896 A1 | 6/2016 |

\* cited by examiner (a)

(b)

ACCOMMODATIVE INTRAOCULAR LENS

TECHNICAL FIELD

The present invention relates to an accommodative intraocular lens to be inserted into a lens capsule whose anterior capsule has been incised in ophthalmic surgery, such as, e.g., extracapsular extraction surgery, performed as cataract surgery, refractive surgery, or presbyopic surgery.

BACKGROUND OF THE INVENTION

Usually, focus adjustment of a human eye is performed by varying the thickness of the lens.

As shown in FIG. 11, a lens L is a transparent lens having a convex shape with a diameter of about 9 mm to about 11 mm and a thickness of about 4 mm to about 5 mm. The lens L is fixed to the ciliary body C via the Zinn's zonule Z in a state of being wrapped with a transparent lens capsule S behind the iris I, and adjusts the focus mainly by changing the curvature of the front surface of the lens L in accordance with the movement of the ciliary body C at the time of the focus adjustment.

The specific adjustment mechanism will be explained. For example, when looking at the distance, as shown in (b) of FIG. 11, the ciliary muscle Cm of the ciliary body C is relaxed, and the ciliary body C is in a position in which it is retracted in a direction away from the lens capsule S. In this condition, relatively strong tension is generated in the Zinn's zonule Z positioned between the ciliary body C and the lens capsule equatorial portion Se. With this, the lens capsule equatorial portion Se is pulled radially outward. Accordingly, the curvature of the front surface of the lens L in the lens capsule S is reduced to perform the focus adjustment at the time of distance vision On the other hand, when accommodative efforts are made to see nearby objects, as shown in (a) of FIG. 11, the ciliary muscle Cm of the ciliary body C contracts, and the ciliary body C protrudes centripetally (in the direction toward the lens capsule equatorial portion Se), so that the ciliary body C is positioned in the direction close to the lens capsule S. As a result, the tension of the Zinn's zonule Z is weakened, so that the curvature of the front surface of the lens L is increased due to the elasticity inherent in the lens L to perform the focus adjustment at the time of near vision.

As the ciliary muscle Cm of the ciliary body C contracts and relaxes as described above, focus adjustment is performed mainly by changing the curvature of the anterior surface of the lens L to refract the light entering the eye. Note that in this adjustment mechanism, it has been found that the contractile function and relaxant function of the ciliary body C by the ciliary muscle Cm are relatively well maintained even with advancing age. However, on the other hand, it has been found that the cortex and nucleus, which are contents of the lens L, harden and lose flexibility when advancing age, and the curvature of the anterior surface of the lens L becomes difficult to change, thereby losing the ability to adjust the focal point voluntarily from the distance vision to the near vision (this is called "presbyopia").

Incidentally, diseases occurring in the lens L include a disease called a cataract which becomes cloudy mainly due to aging, and many patients undergo cataract surgery for treating the cataract. In this operation, a circular hole is usually incised in an anterior capsule Sf. Then, the contents of the cloudy lens L are extracted therefrom by phacoemulsification and the intraocular lens is inserted into the lens capsule S while leaving only the transparent lens capsule S in an incised state. Cataract surgery by this method is currently administered to more than 1 million patients per year in Japan and more than 3 million patients per year in the United States. Various intraocular lenses have been proposed as intraocular lenses used in this surgery.

For example, the intraocular lens described in Patent Document 1 is called a so-called accommodative intraocular lens. The intraocular lens is composed of an optical portion (optical lens 42) and a support portion (optical lens positioning component 46). The support portion is provided with a front portion, a rear portion, and a curved portion connecting the front portion and the rear portion. The optical portion and the front portion of the support portion are connected via haptic arms. With this configuration, the support portion deflects in accordance with the movement of the lens capsule at the time of distance vision and near vision, so that the optical portion is configured to move in the anterior-posterior direction (see FIG. 7 and FIG. 8 of Patent Document 1).

PRIOR ART DOCUMENT

Patent Document

Patent Document 1: Translation of PCT Patent Publication No. 2006-503661

SUMMARY OF THE INVENTION

Problems to be Solved by the Invention

However, the accommodative intraocular lens is merely configured such that the support portion (particularly, the curved portion) expands or contracts radially in response to the movements of the lens capsule. For this reason, the above-mentioned accommodative intraocular lens exhibits only a weak focus adjustment function, and was difficult to exert a practical focus adjustment function that does not require glasses from reading to driving. Under the circumstance, there has been a great demand for an accommodative intraocular lens capable of capturing a minute movement of a lens capsule caused by a weak force such as contraction or relaxation of a ciliary muscle, amplifying the movement into a relatively large movement of an optical portion, and expressing a practical focus adjustment function.

This will be explained in more detail. A lens capsule of a physiologically normal lens merely moves by up to 0.4 mm even at a position where the lens capsule moves best (i.e., the central portion of the anterior capsule). The central portion of the anterior capsule is incised in a circular shape with a size of about 5 mm in diameter in surgery, and it has been found that the remaining lens capsule near the equator of the lens merely moves by about 0.25 mm even if it moves well. Thus, a simple movement of the optical portion of the accommodative intraocular lens in accordance with the movement of the lens capsule merely produces a weak accommodative power.

For example, when the accommodative power is calculated by a ray tracing method by replacing the total lateral eye lens and the homogeneous nucleus lens of the Glustrand with a 22 diopter refractive power, which is a typical accommodative intraocular lens power, it has been found that only a 0.5 diopter accommodative power is produced when the optical portion of the accommodative intraocular lens is moved by 0.25 mm.

Three diopters are required to perform focus adjustment from a distance of 33 cm in front of an eye suitable for reading to infinity. On the other hand, it has been found that a human eye has a pseudo-accommodation force of about 2 diopters due to a pinhole effect due to contraction of a pupil and a multifocal nature of a cornea. Therefore, it is enough that a focus adjustment force generated by an accommodative intraocular lens is only 1 diopter. The addition of 1 diopter of an accommodative intraocular lens to 2 diopters of a pseudo-accommodative force provides 3 diopters, which provides a practical minimum focus adjustment force from reading to a personal computer operation and a vehicle operation.

When the moving amount of the optical portion of the accommodative intraocular lens required for an accommodative intraocular lens having a typical 22 diopters to produce an accommodative power of 1 diopter or more is calculated by a ray tracing method using a Glustrand model eye, it can be confirmed that the optical portion has to move by 0.5 mm or more.

Therefore, in order for the accommodative intraocular lens to exert a practical focusing adjustment power, it is required to have any amplifying function of capturing a minute movement of a lens capsule of about 0.25 mm and amplifying the minute movement to a movement of the optical portion of 0.5 mm or more.

The present invention has been made in view of the above-mentioned technical background, and an object of the present invention is to provide an accommodative intraocular lens capable of capturing a minute movement of a lens capsule, amplifying the movement to a large movement of an optical portion, and thus exerting a practical focus adjustment function.

Means for Solving the Problem

In order to achieve the above-described object, the present invention provides an accommodative intraocular lens to be placed in a lens capsule whose anterior capsule has been incised in ophthalmic surgery, and is provided with an optical portion and one or a plurality of support portions arranged around the optical portion to support the optical portion. The support portion is composed of an anterior support portion provided in a manner as to come into contact with an inner surface of an anterior capsule and a posterior support portion provided in a manner as to come into contact with an inner surface of a posterior capsule. The anterior support portion presses the anterior capsule and the posterior support portion presses the posterior capsule by an elastic force of the support portion. The anterior support portion extends radially inward and forward from a base end portion connected to the posterior support portion and then extends radially inward and backward, and a tip end portion of the anterior support portion is connected to a peripheral portion of the optical portion. When the lens capsule is in a distance vision state, as a pressing force on the anterior support portion by the anterior capsule increases, the anterior support portion deflects backward while maintaining a radial position of the base end portion. As a result, the tip end portion of the anterior support portion moves backward while maintaining its radial position, so that the optical portion moves backward accordingly. On the other hand, when the lens capsule is in a near vision state, when the pressing force on the anterior support portion by the anterior capsule decreases, the anterior support portion returns forward by the elastic force while maintaining the radial position of the base end portion. As a result, the tip end portion of the anterior support portion moves forward while maintaining its radial position, so that the optical portion moves forward accordingly.

According to this, the anterior support portion presses the inner surface of the anterior capsule and the posterior support portion presses the inner surface of the posterior capsule by the elastic force of the support portion. As a result, the peripheral portion of the lens capsule equatorial portion expands in the anterior-posterior direction, so that the lens capsule equatorial portion expands. At the same time, the lens capsule equatorial portion moves centripetally, thereby reducing the diameter of the lens capsule equatorial portion. With this, the Zinn's zonule is pulled in both directions toward the capsular side and the ciliary side, providing sustainable tension to the Zinn's zonule. This allows the Zinn's zonule to transmit slight contraction and relaxation of the ciliary muscle of the ciliary body to the lens capsule.

Further, when the lens capsule is in a distance vision state, when the pressing force on the anterior support portion by the anterior capsule increases, the anterior support portion largely deflects backward. As a result, the tip end portion of the anterior support portion moves backward by a larger amount than the moving amount of the anterior capsule. Accordingly, the optical portion can move backward largely. On the other hand, when the lens capsule is in a near vision state, when the pressing force on the anterior support portion by the anterior capsule decreases, the anterior support portion returns to its original state by the elastic force. As a result, the tip end portion of the anterior support portion moves forward by a larger amount than the moving amount of the anterior capsule. Accordingly, the optical portion can move forward largely. For this reason, minute movement of the lens capsule can be captured and amplified to a large movement of the optical portion, which in turn can exert a practical focus adjustment function.

Further, the support portion may be provided with a regulating member for maintaining the radial position of the base end portion of the anterior support portion. For example, the regulating member may be formed in such a manner as to circumferentially connect the base end portions of the anterior support portions adjacent to each other. Alternatively, the regulating member may be formed in such a manner as to protrude at a height position of the lens capsule equatorial portion on the outer surface of the support portion. This restricts the anterior support portion from moving radially outward of the base end portion. This ensures that the anterior support portion deflects backward and returns forward while maintaining the radial position of the base end portion.

The anterior support portion may have a longitudinally extending hole portion. According to this, the anterior support portion has a shape which is lower in stiffness than the posterior support portion and is easily deflected. Therefore, it is possible to reliably deflect backward or return forward while maintaining the radial position of the base end portion.

The anterior support portion may be formed to be thinner than the posterior support portion. According to this, the anterior support portion has a shape which is lower in stiffness than the posterior support portion and is easily bent. Therefore, the anterior support portion can be reliably deflected backward or can return forward while maintaining the radial position of the base end portion.

Further, when the lens capsule is in a near vision state, the tip end portion of the anterior support portion may be positioned forward of the center position of the lens capsule equatorial portion. On the other hand, when the lens capsule is in a distance vision state, the tip end portion of the anterior support portion may be positioned backward of the center position of the lens capsule equatorial portion. According to this, since the optical portion moves backward or forward more largely, the focus adjustment function can be exerted more effectively.

The anterior support portion may have one or a plurality of notches extending in a width direction. According to this, the anterior support portion can be easily deflected or returned to its original state due to the notch. Therefore, the focus adjustment function can be more effectively exerted by minute movement of the lens capsule.

Effects of the Invention

According to the present invention, the elastic force of the support portion causes the anterior support portion to press against the inner surface of the anterior capsule and the posterior support portion to press against the inner surface of the posterior capsule. With this, the peripheral portion of the lens capsule equatorial portion extends and expands in the anterior-posterior direction to expand the lens capsule equatorial portion. At the same time, the lens capsule equatorial portion moves centripetally, so that the diameter of the lens capsule equatorial portion reduces. With this, the Zinn's zonule is pulled in both directions toward the capsular side and the ciliary side, which in turn provides sustainable tension to the Zinn's zonule. This allows the Zinn's zonule to transmit slight contraction and relaxation of the ciliary muscle of the ciliary body to the lens capsule.

Further, when the lens capsule is in a distance vision state, as the pressing force on the anterior support portion by the anterior capsule increases, the anterior support portion is largely deflected backward. As a result, the tip end portion of the anterior support portion moves backward by a larger amount than the moving amount of the anterior capsule, so that the optical portion can move backward largely. On the other hand, when the lens capsule is in a near vision state, as the pressing force on the anterior support portion by the anterior capsule decreases, the anterior support portion returns to its original state by the elastic force. As a result, the tip end portion of the anterior support portion moves forward by a larger amount than the moving amount of the anterior capsule. Accordingly, the optical portion can move forward largely. For this reason, minute movement of the lens capsule can be captured and amplified to a large movement of the optical portion, so that a practical focus adjustment function can be exerted.

The weak contraction and relaxation of the ciliary body's ciliary muscle are transmitted via the Zinn's zonule to the lens capsule under a condition in which the lens capsule is tensioned and the lens capsule is flexible and deformable. Therefore, in both the near vision and the distance vision, it is possible to capture the minute movement of the lens capsule and amplify it to a large movement in the anterior-posterior direction of the optical portion, so that it is possible to exert a practical focus adjustment function.

EMBODIMENTS FOR CARRYING OUT THE INVENTION

First Embodiment

Next, with reference to FIG. 1 to FIG. 5, a first embodiment of an accommodative intraocular lens according to the present invention (hereinafter referred to as this lens 1) will be described. Note that the following description will be made assuming that the upper side of each drawing denotes a front side of a human eye, and the lower side of each drawing denotes a rear side of the human eye.

Figure 1:
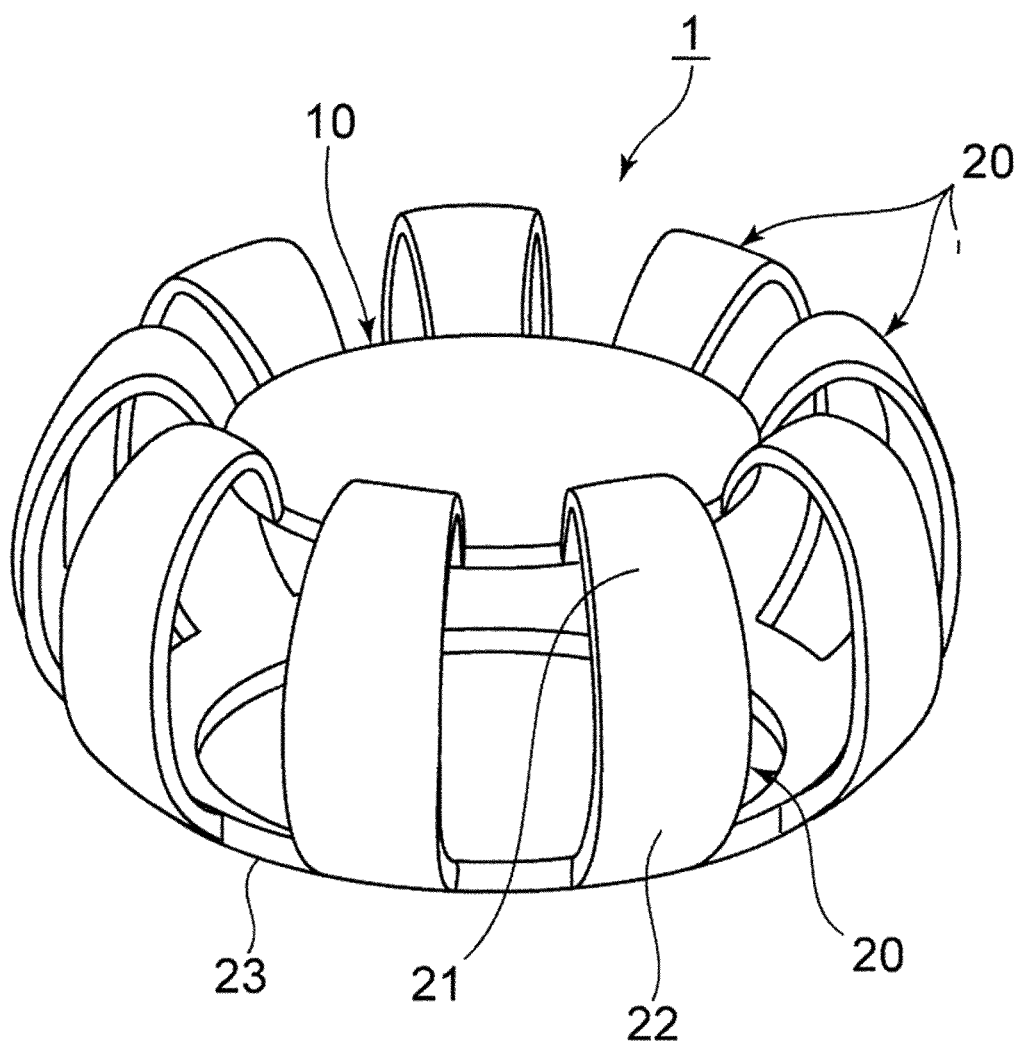
FIG. 1 is a perspective view of an accommodative intraocular lens according to a first embodiment of the present invention.
Figure 2:
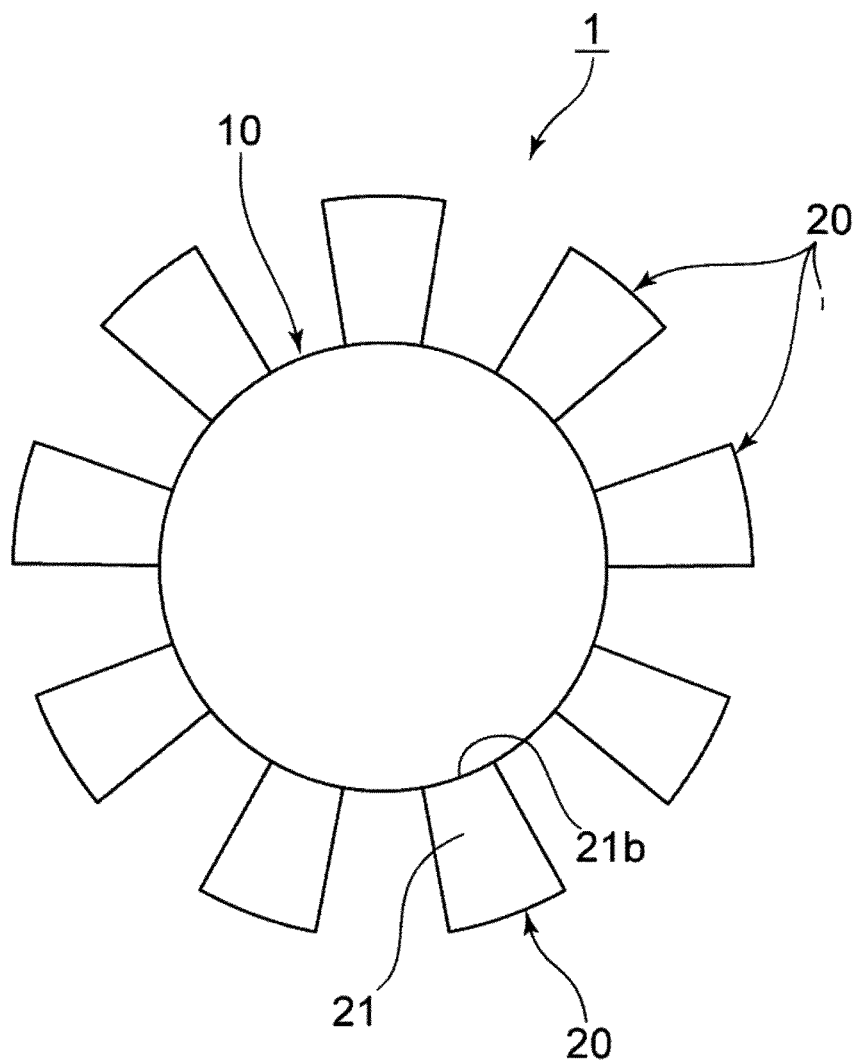
FIG. 2 is a plan view of the accommodative intraocular lens of FIG. 1.
Figure 3:
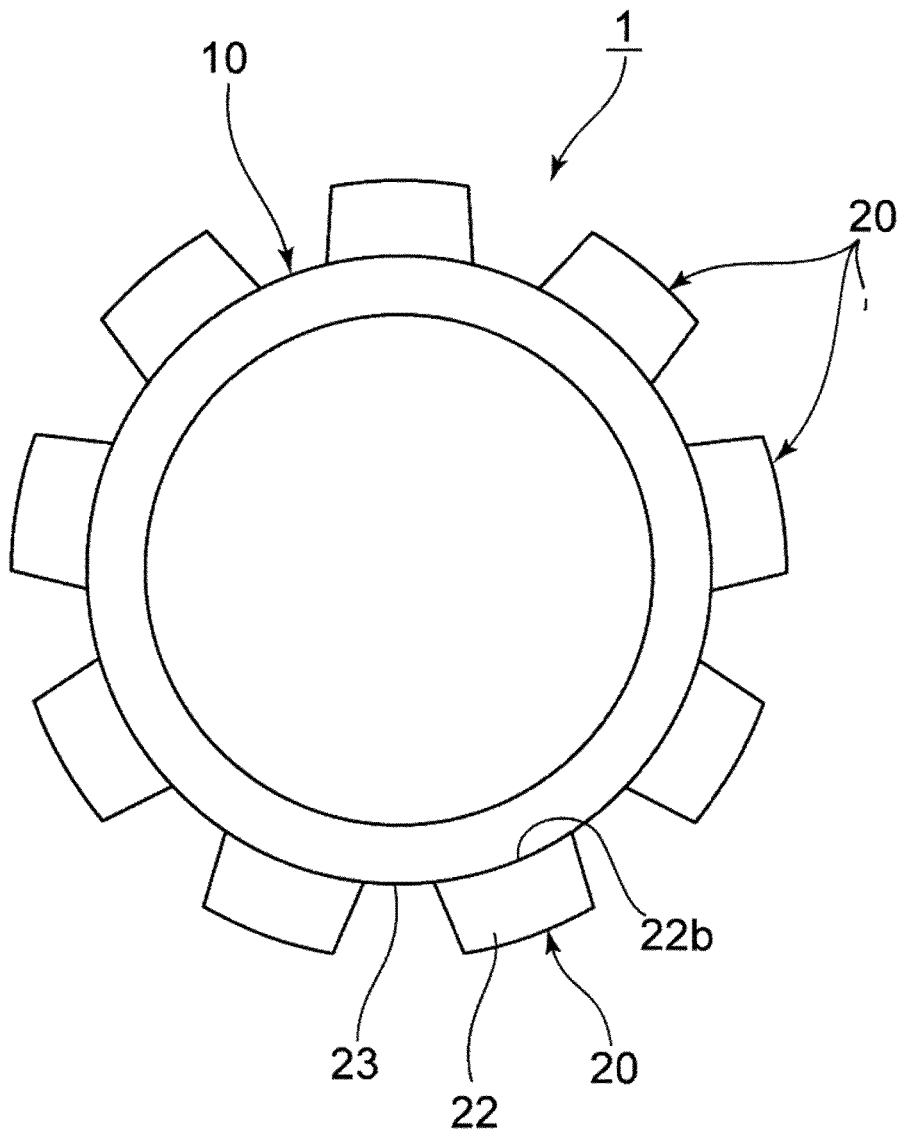
FIG. 3 is a bottom view of the accommodative intraocular lens of FIG. 1.
Figure 4:
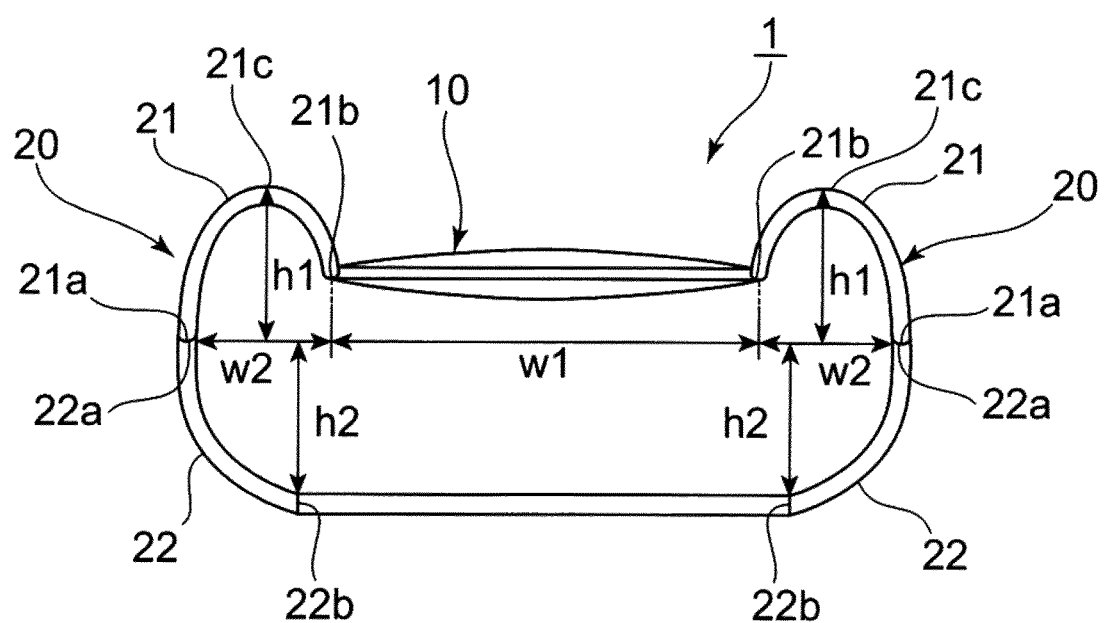
FIG. 4 is a longitudinal cross-sectional view of the accommodative intraocular lens of FIG. 1.
Figure 5:
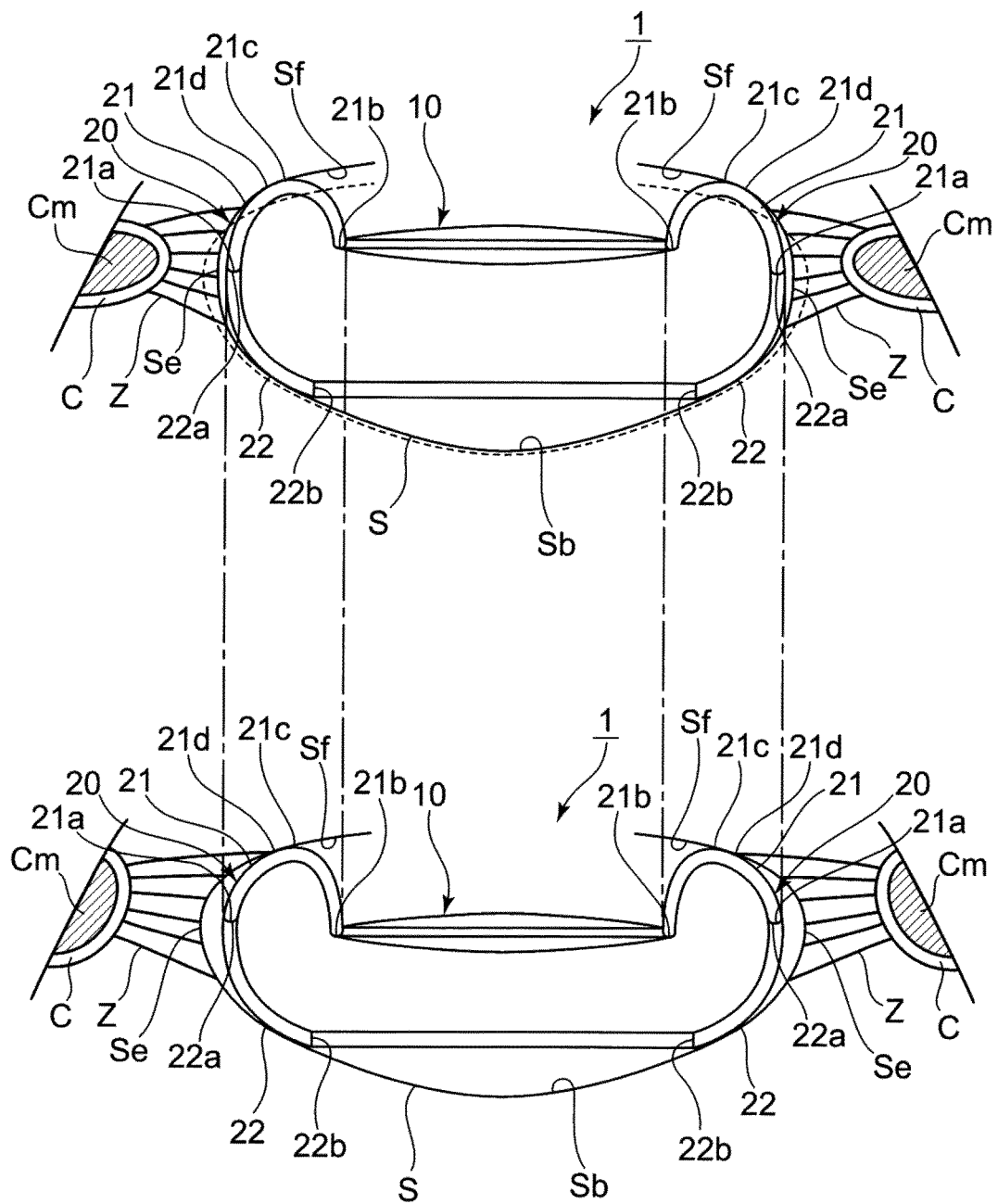
FIG. 5 is a vertical cross-sectional view of the accommodative intraocular lens of FIG. 1 showing near and distance vision states.

As shown in FIG. 1 to FIG. 4, this lens 1 is provided with an optical portion 10 and nine support portions 20 arranged around the optical portion 10 to support the optical portion 10, and is used by being installed in a lens capsule S whose anterior capsule has been incised in ophthalmic surgery as shown in FIG. 5.

The optical portion 10 is a convex lens made of a synthetic resin material, such as, e.g., silicone, acryl, hydrogel, PMMA, HEMA, and hydro-polymer, and has a diameter w1 of 4 mm to 7 mm in a plan view. The shape and material of the optical portion 10 are not limited to these, and may be another shape and material.

The support portions 20 are each composed of an anterior support portion 21 to be installed in a manner as to come into contact with an inner surface of an anterior capsule Sf and a posterior support portion 22 to be installed in a manner as to come into contact with an inner surface of a posterior capsule Sb, and are arranged side by side at regular intervals along the circumferential direction of this lens 1.

The support portions 20 are each formed to have a width of 1 mm in the circumferential direction of this lens 1, a total height of 3.5 mm in the anterior-posterior direction of this lens 1, and a thickness of 0.2 mm. The height of this lens 1 is set such that this lens slightly moves in the anterior-posterior direction when this lens 1 is installed in the lens capsule S.

The support portion 20 is made of a flexible material having a predetermined elastic force (e.g., a rubber hardness (A scale) of 20 degrees to 90 degrees, preferably 40 degrees to 70 degrees). The support portion 20 is configured such that, when installed in the lens capsule S, the anterior support portion 21 deflects backward in response to the movement of the lens capsule S. The concrete deflection behavior of the support portion 20 will be described later. Since the force of the ciliary muscle is said to be 2 gf, the reaction force of 0.5 gf to 5 gf when the part where the anterior support portion 21 and the anterior capsule Sf are in contact with each other is moved by 0.5 mm is optimal, and the reaction force is expressed as a spring force of 9.8 N/m to 98 N/m.

The anterior support portion 21 is formed in such a manner as to extend from a base end portion 21a connected to the posterior support portion 22 while being gently curved radially inward and forward, and then sharply curved at a curved portion 21c and gradually curved radially inward and backward, so that the tip end portion 21b is connected to the peripheral portion of the optical portion 10. The anterior support portion 21 is formed to have a height h1 of 1.25 mm to 2.25 mm in the anterior-posterior direction (the height from the base end portion 21a to the curved portion 21c) and a depth w2 of 1.0 mm to 2.75 mm in the radial direction (the depth from the base end portion 21a to the tip end portion 21b).

The posterior support portion 22 is formed in such a manner as to extend from a base end portion 22a connected to the anterior support portion 21 while being gently curved radially inward and backward. The posterior support portion 22 is formed to have a height h2 of 1.0 mm to 2.0 mm in the anterior-posterior direction (height from the base end portion 22a to the tip end portion 22b). In the posterior support portions 22, the adjacent tip end portions 22b are connected each other via a connecting portion 23, so that the posterior support portions are stably installed on the inner surface of the posterior capsule Sb when installed in the lens capsule S.

The boundary portion between the anterior support portion 21 (base end portion 21a) and the posterior support portion 22 (base end portion 22a) refers to a radially outermost portion of the support portion 20. When the vicinity of the boundary portion between the anterior support portion 21 and the posterior support portion 22 is straight in the anterior-posterior direction, the central portion of the straight portion is regarded as the boundary portion. In FIG. 4 and FIG. 5, an imaginary line for clarifying the boundary portion is illustrated.

Next, how to install this lens 1 in a lens capsule S will be described.

In ophthalmic surgery, this lens 1 is inserted into the lens capsule S in which the anterior capsule Sf has been incised by an injector or tweezers. Thereafter, the optical portion 10 is installed so that the anterior support portion 21 (anterior capsule contact portion 21d) of this lens 1 comes into contact with the inner surface of the anterior capsule Sf of the lens capsule S, the posterior support portion 22 comes into contact with the inner surface of the posterior capsule Sb of the lens capsule S, and the optical portion 10 becomes perpendicular to the anterior-posterior direction at a height position near the equator of the lens capsule S. At this time, the anterior capsule contact portion 21d of the anterior support portion 21 is located on the base end portion 21a side than the curved portion 21c.

At this time, the length of this lens 1 is formed to be slightly longer than the length of the lens capsule S in the anterior-posterior direction. Therefore, as shown in FIG. 5, this lens is in a state of being slightly deflected in the anterior-posterior direction in the lens capsule S, so that the anterior support portion 21 presses the anterior capsule Sf and the posterior support portion 22 presses the posterior capsule Sb by the elastic force of the support portion 20.

Thus, the lens capsule equatorial portion Se expands as the peripheral portion of the lens capsule equatorial portion Se attempts to extend and expand in the anterior-posterior direction, and at the same time, the lens capsule equatorial portion Se moves radially inward centripetally, so that the diameter of the lens capsule equatorial portion Se reduces. As a result, the Zinn's zonule Z is pulled in both directions toward the lens capsule S side and the ciliary body C side, and the tension is continuously applied to the Zinn's zonule Z, and as a result, the tension is applied to the lens capsule S. For this reason, the Zinn's zonule Z can transmit slight contraction and relaxation of the ciliary muscle Cm of the ciliary body C to the lens capsule S.

Next, with reference to FIG. 5, the operation of this lens 1 in a distance vision state and in a near vision state will be described.

In FIG. 5, the upper figure is a vertical cross-sectional view showing the near vision state of this lens 1, and the lower figure is a vertical cross-sectional view showing the distance vision state of this lens 1. The dotted line in the upper figure of FIG. 5 indicates a virtual line of the lens capsule S in a distance vision state. The alternate long and short dash lines in the upper and lower figures of FIG. 5 indicate that the radial position of the base end portion 21a in the upper figure coincides with that in the lower figure and the redial position of the tip end portion 21b of the anterior support portion 21 in the upper figure coincides with that in the lower figure.

When the lens capsule S is in the distance vision state, as shown in the upper figure of FIG. 5, from the state in which the ciliary muscle Cm of the ciliary body C contracts and protrudes radially inward in a centripetal manner and the degree of tension of the Zinn's zonule Z is reduced, as shown in the lower figure of FIG. 5, it becomes a state in which the ciliary muscle Cm of the ciliary body C relaxes, so that the ciliary body C is positioned radially outward, thereby pulling the lens capsule S via the Zinn's zonule Z to increase the degree of tension of the Zinn's zonule Z. Therefore, the tension of the peripheral portion of the lens capsule equatorial portion Se becomes high, so that the pressing force of the anterior support portion 21 by the anterior capsule Sf increases and the pressing force of the posterior support portion 22 by the posterior capsule Sb increases. This causes the backward movement of the anterior capsule Sf while the lens capsule S is being spread in the radial direction.

At this time, when the anterior capsule contact portion 21d of the anterior support portion 21 receives a pressing force from the anterior capsule Sf radially inward and backward, the base end portion 21a of the anterior support portion 21 serves as a fulcrum, and the anterior capsule contact portion 21d moves radially inward and backward so as to be pushed by the anterior capsule Sf. At this time, the base end portion 21a of the anterior support portion 21 maintains the position in the radial direction and in the anterior-posterior direction in the lens capsule S, and the tip end portion 21b of the anterior support portion 21 maintains the position in the radial direction by the optical portion 10. For this reason, it becomes a state in which the entire anterior support portion 21 is largely deflected backward, so that the tip end portion 21b of the anterior support portion 21 moves backward by a larger amount than the moving amount of the anterior capsule Sf. Accordingly, the optical portion 10 can also move backward by a larger amount.

On the other hand, when the lens capsule S is in a near vision state, as shown in the lower figure of FIG. 5, the ciliary muscle Cm of the ciliary body C relaxes and the ciliary body C is located radially outward, thereby pulling the lens capsule S via the Zinn's zonule Z. As a result, from the state in which the degree of tension of the Zinn's zonule Z is increased (distance vision state), it becomes a state in which the ciliary muscle Cm of the ciliary body C is contracted and protrudes radially inward as shown in the upper figure of FIG. 5 and the degree of tension of the Zinn's zonule Z is decreased. Therefore, since the tension of the peripheral portion of the lens capsule equatorial portion Se is reduced, the pressing force of the anterior support portion 21 and the posterior support portion 22 by the anterior capsule Sf and the posterior capsule Sb is lowered.

At this time, the anterior support portion 21 of this lens 1 moves radially outward and forward with the base end portion 21a of the anterior support portion 21 serving as a fulcrum so that the anterior capsule contact portion 21d pushes back the anterior capsule Sf by the elastic force of the anterior support portion 21. At this time, the base end portion 21a of the anterior support portion 21 maintains the position in the radial direction and the anterior-posterior direction in the lens capsule S, and the tip end portion 21b of the anterior support portion 21 maintains the position in the radial direction. Therefore, by returning the anterior support portion 21 to the original state (the near vision state in the upper figure of FIG. 5), the tip end portion 21b of the anterior support portion 21 moves forward by a larger amount than the moving amount of the anterior capsule Sf. In accordance with it, the optical portion 10 can also move forward by a larger amount.

In this respect, in a conventional accommodative intraocular lens, when the lens capsule S is in a distance vision state or in a near vision state, when the pressing force of the anterior capsule Sf against the support portion 20 in the radially inward and backward direction increases or decreases, the entire support portion 20 expands or shrinks in the radial direction, and the minute movement of the lens capsule S is merely transmitted to the optical portion 10 as it is. Thus, the minute movement of the lens capsule S is not configured to be amplified to the movement of the optical portion 10 as in the present invention. Therefore, the optical portion 10 cannot move backward or forward greatly, so that practical focus adjustment function cannot be exerted.

However, in this lens 1, as described above, the tip end portion 21b of the anterior support portion 21 moves in the anterior-posterior direction by a larger amount than the moving amount of the anterior capsule Sf. In accordance with it, the optical portion 10 also moves in the anterior-posterior direction by a larger amount. Therefore, it is possible to detect the minute movement of the lens capsule S and amplify it to a large movement of the optical portion 10 in the anterior-posterior direction, so that it is possible to exert a practical focus adjustment function.

According to the calculation on the figures in this embodiment, this lens 1 has an amplifying function of 2 to 2.5 times, the movement of the anterior capsule Sf of 0.25 mm is amplified to the movement of the optical portion 10 of 0.5 mm to 0.625 mm, and the adjustment of 1.0 to 1.25 diopters, which is a practical adjustment force, can be obtained when the power of the optical portion 10 is 22 diopters.

In particular, in this embodiment, in the anterior support portion 21, the tip end portion 21b is positioned forward of the center position of the lens capsule equatorial portion Se when the lens capsule S is in a near vision state, and the tip end portion 21b is positioned backward of the center position of the lens capsule equatorial portion Se when the lens capsule S is in a distance vision state. Therefore, since the optical portion 10 moves backward or forward more greatly, the focus adjustment function can be exerted more effectively.

It should be noted that the state in which the base end portion 21a of the anterior support portion 21 maintains the position in the radial direction includes not only the state in which the position in the radial direction is completely maintained, but also the state in which the base end portion 21a moves in the radial direction within 10% of the entire diameter of this lens 1. It should be also noted that the state in which the base end portion 21a of the anterior support portion 21 maintains the position in the anterior-posterior direction includes not only the state in which the position in the anterior-posterior direction is completely maintained, but also the state in which it moves in the anterior-posterior direction within 10% of the entire height in the anterior-posterior direction of this lens 1. It should be further noted that the state in which the tip end portion 21b of the anterior support portion 21 maintains the radial position includes not only the state in which the radial position is completely maintained, but also the case in which the tip end portion 21b moves radially within 8% of the entire diameter of this lens 1.

Second Embodiment

Figure 6:
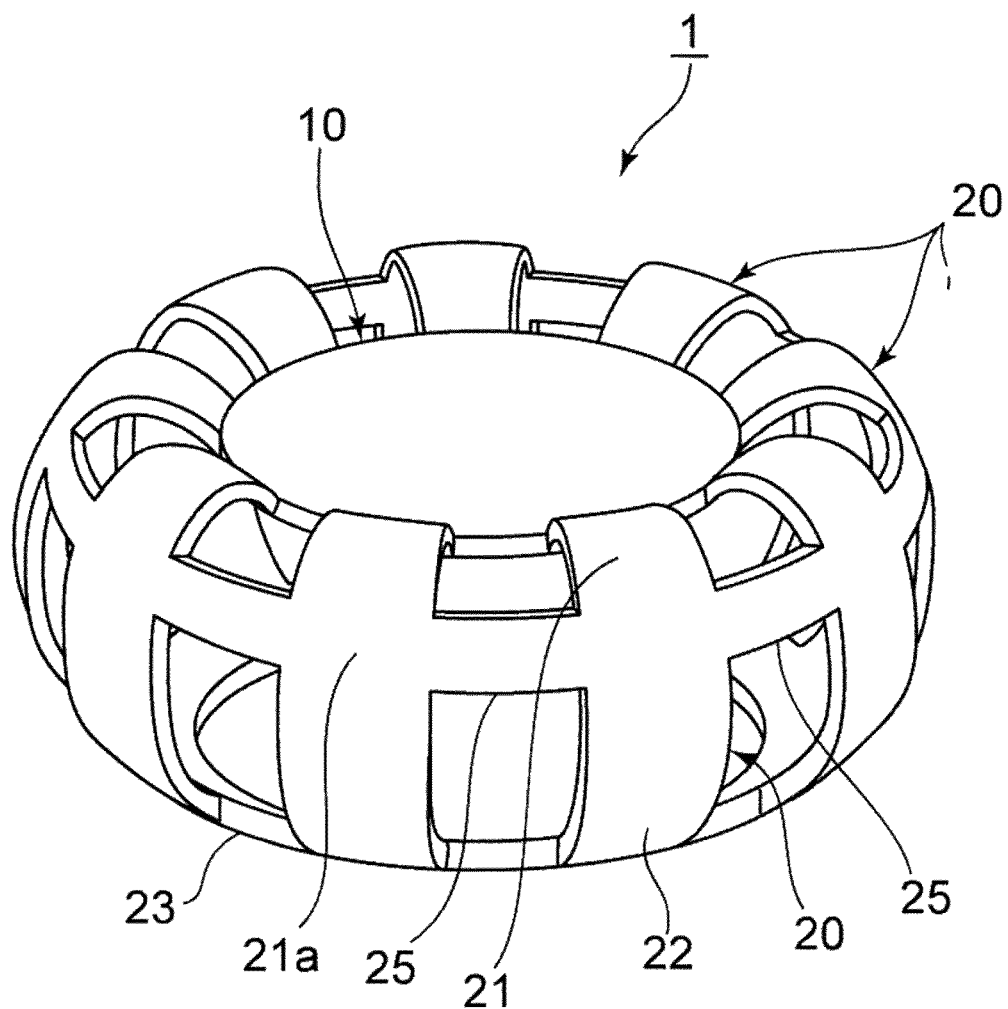
FIG. 6 is a perspective view of the accommodative intraocular lens according to a second embodiment.

Next, a second embodiment of this lens 1 will be described with reference to FIG. 6. In the following description, only configurations different from the above-described embodiment will be described, and the same reference numeral will be given to the same configuration without description.

In this embodiment, the anterior support portion 21 is provided with a regulating member 25 for maintaining the radial position of the base end portion 21a connected to the posterior support portion 22. The regulating member 25 is formed in such a manner that the base end portions 21a of the adjacent anterior support portions 21 are circumferentially connected to each other.

This restricts the anterior support portion 21 from moving radially outward of the base end portion 21a, so that it is possible to reliably deflect the anterior support portion 21 backward or return forward while maintaining the position of the base end portion 21a in the radial direction.

Third Embodiment

Figure 7:
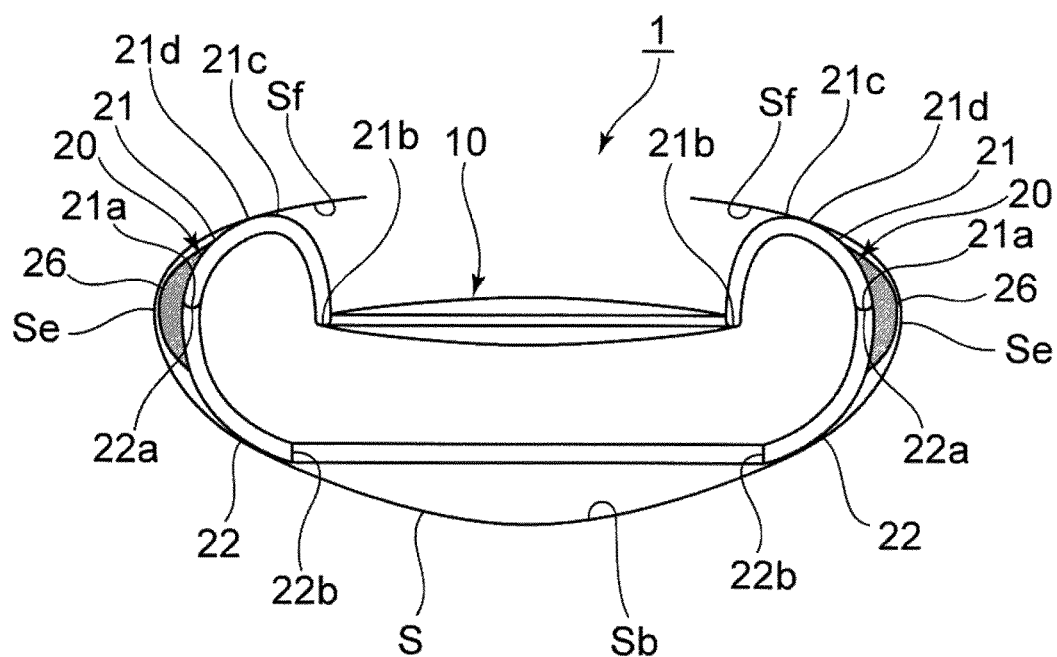
FIG. 7 is a vertical cross-sectional view of the accommodative intraocular lens according to a third embodiment.

Next, a third embodiment of this lens 1 will be described with reference to FIG. 7.

In this embodiment, the anterior support portion 21 is provided with a regulating member 26 for maintaining the radial position of the base end portion 21a connected to the posterior support portion 22. The regulating member 26 is formed in such a manner as to project radially outward at a height position of the lens capsule equatorial portion Se on the outer peripheral surface of the anterior support portion 21, and is arranged so as to come into contact with the lens capsule equatorial portion Se.

This restricts the anterior support portion 21 from moving radially outward of the base end portion 21a, so that it is possible to reliably deflect the anterior support portion 21 backward or return forward while maintaining the position of the base end portion 21a in the radial direction.

Fourth Embodiment

Figure 8:
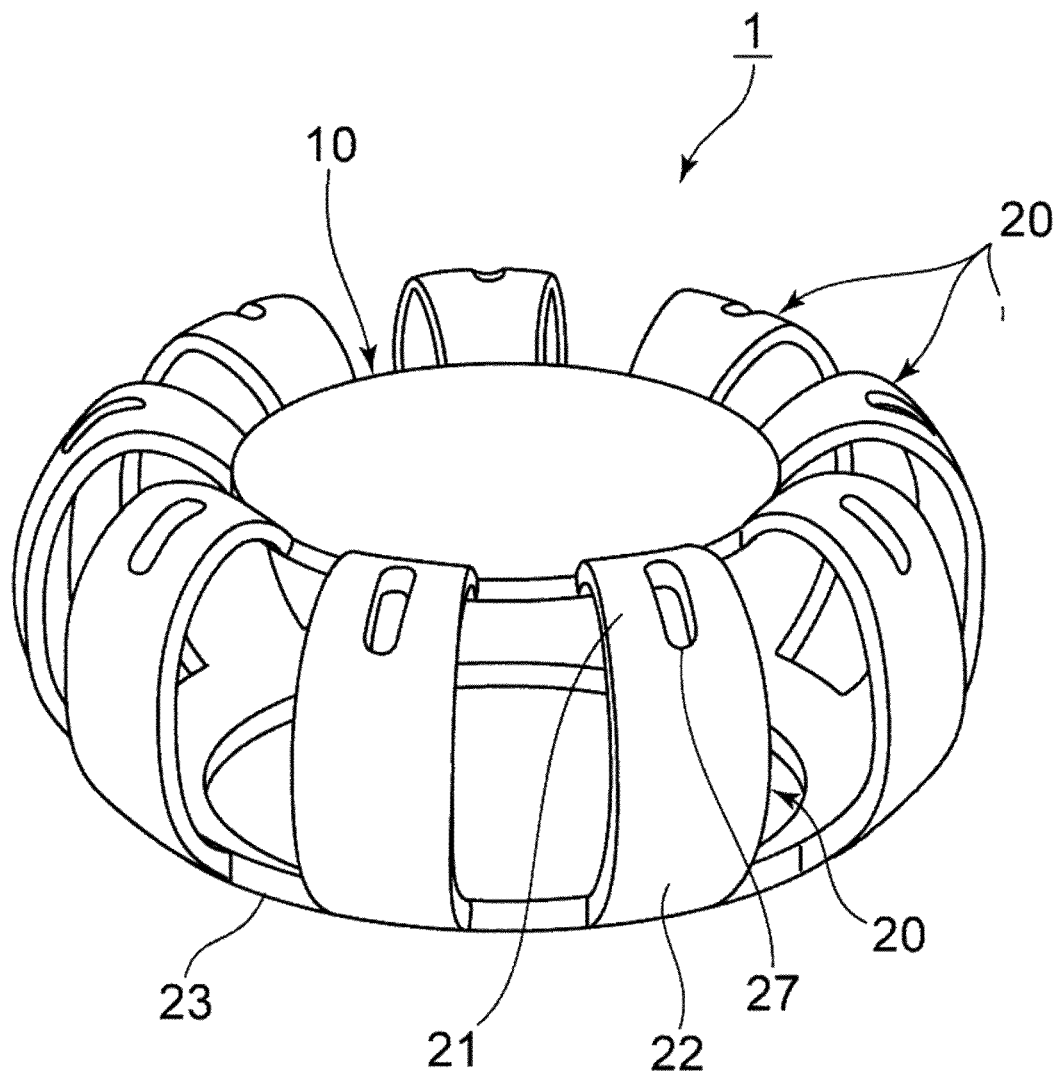
FIG. 8 is a perspective view of a accommodative intraocular lens according to a fourth embodiment.

Next, a fourth embodiment of this lens 1 will be described with reference to FIG. 8.

In this embodiment, the anterior support portion 21 is formed with a longitudinally extending hole 27.

According to this, since the anterior support portion 21 is less rigid than the posterior support portion 22 and is easily deflected, it can be reliably deflected backward or returned forward while maintaining the radial position of the base end portion 21a.

Fifth Embodiment

Figure 9:
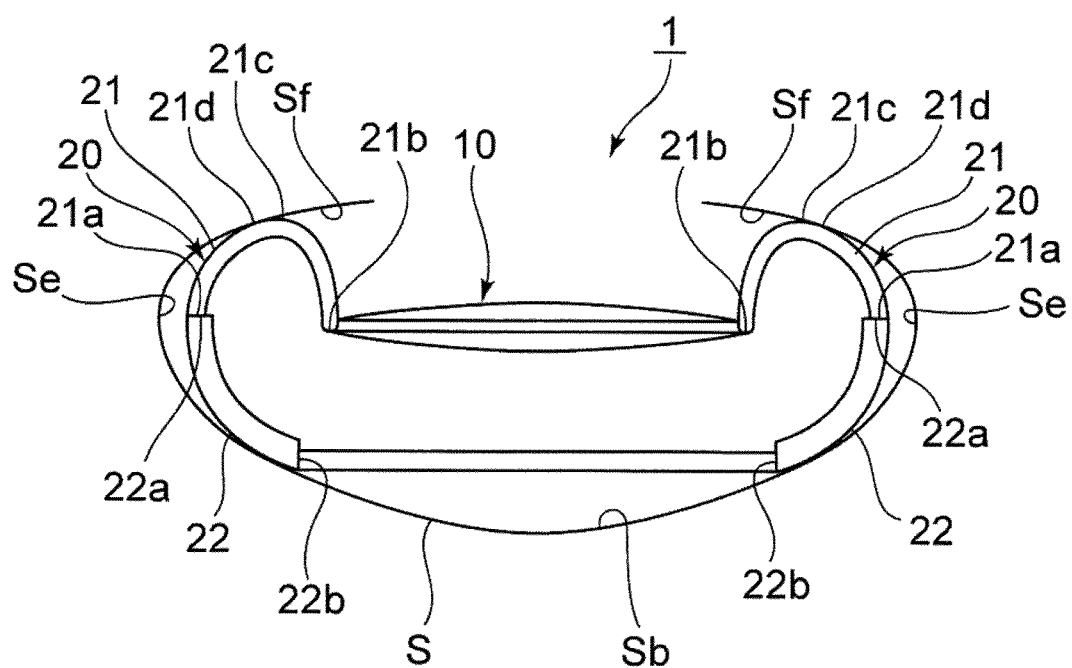
FIG. 9 is a vertical cross-sectional view of the accommodative intraocular lens according to a fifth embodiment.

Next, a fifth embodiment of this lens 1 will be described with reference to FIG. 9.

In this embodiment, the anterior support portion 21 is formed to be thinner than the posterior support portion 22.

According to this, since the anterior support portion 21 is less rigid than the posterior support portion 22 and is easily deflected, it can be reliably deflected backward or be returned forward while maintaining the radial position of the base end portion 21a.

Sixth Embodiment

Figure 10:
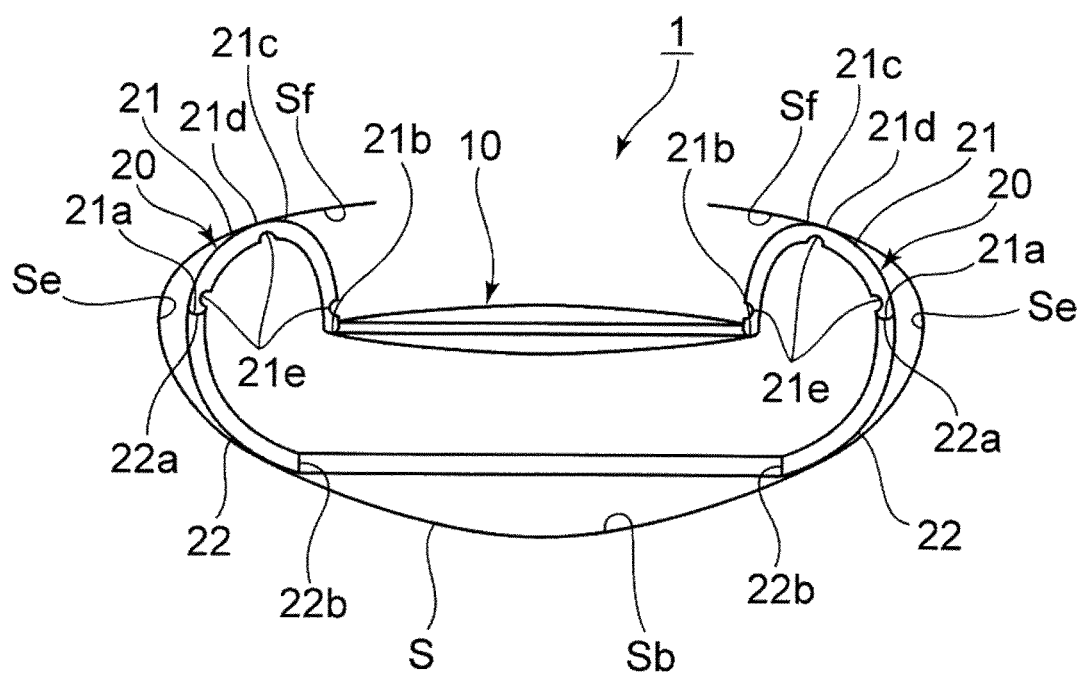
FIG. 10 is a vertical cross-sectional view of the accommodative intraocular lens according to a sixth embodiment.
Figure 11:
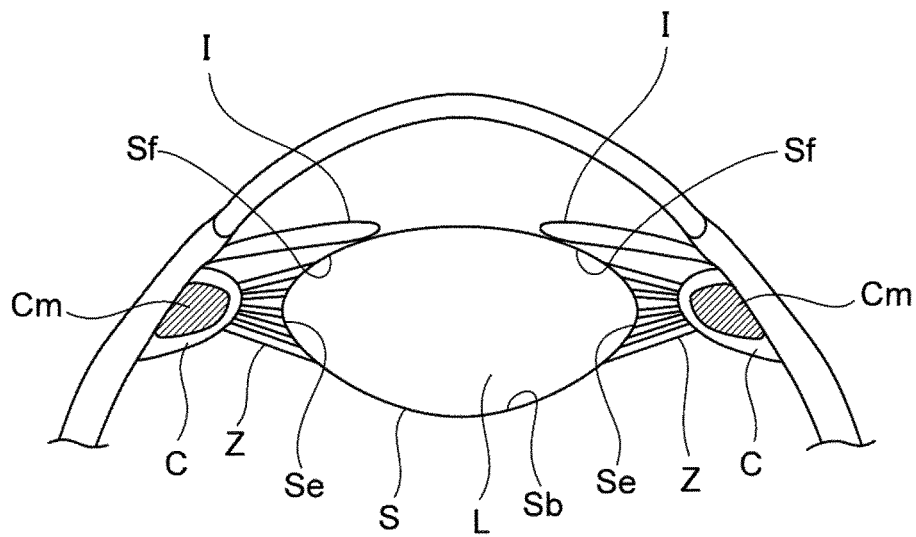
FIG. 11 is a vertical cross-sectional view showing a movement of a human eye during focus adjustment.
Figure 11:
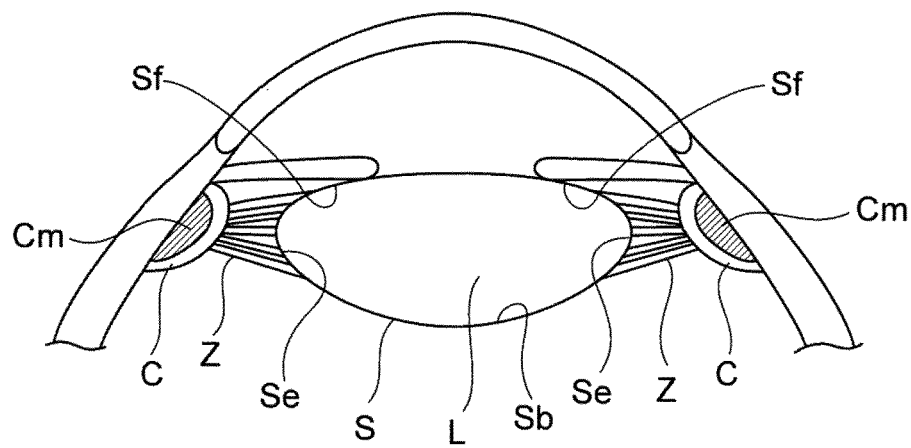

Next, a sixth embodiment of this lens 1 will be described with reference to FIG. 10, In this embodiment, the anterior support portion 21 is formed with notches 21e extending circumferentially on the inner surface of the base end portion 21a connected to the posterior support portion 22, the inner surface of the sharply curved portion 21c, and the outer surface of the tip end portion 21b connected to the optical portion 10 (the surface on which the optical portion 10 exists).

According to this configuration, since the notches 21e function like hinges, the anterior support portion 21 can be easily deflected or returned forward, so that the focus adjustment function can be more effectively exerted than the minute movement of the lens capsule S.

Embodiments of the present invention have been described above with reference to the drawings, but the present invention is not limited to the illustrated embodiments. It should be noted that various modifications and variations can be made to the illustrated embodiments within the same or equivalent scope as the present invention.

EXAMPLES

Figure 12:
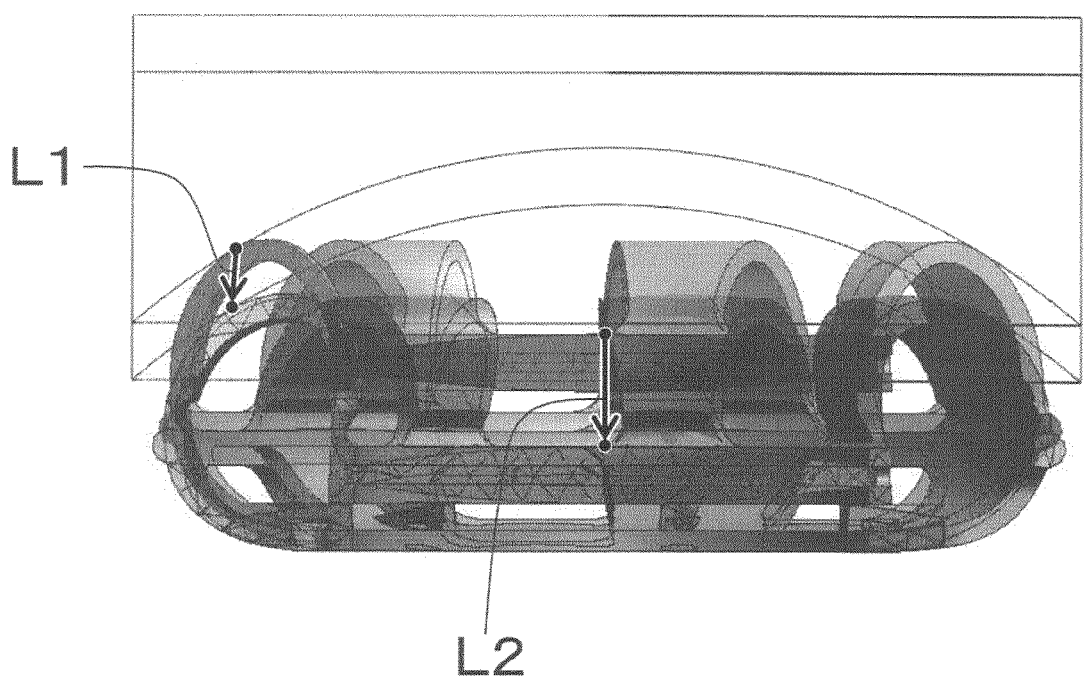
FIG. 12 is a vertical cross-sectional view showing computer a simulation of the accommodative intraocular lens.

The lenses 1 according to the above embodiments were subjected to computer simulations as shown in FIG. 12. In FIG. 12, two curves are drawn on the upper side of this lens 1, which represent the shape of the anterior capsule obtained from the simulated eye of the Gullstrand and the transition of the contacting position.

Figure 13:
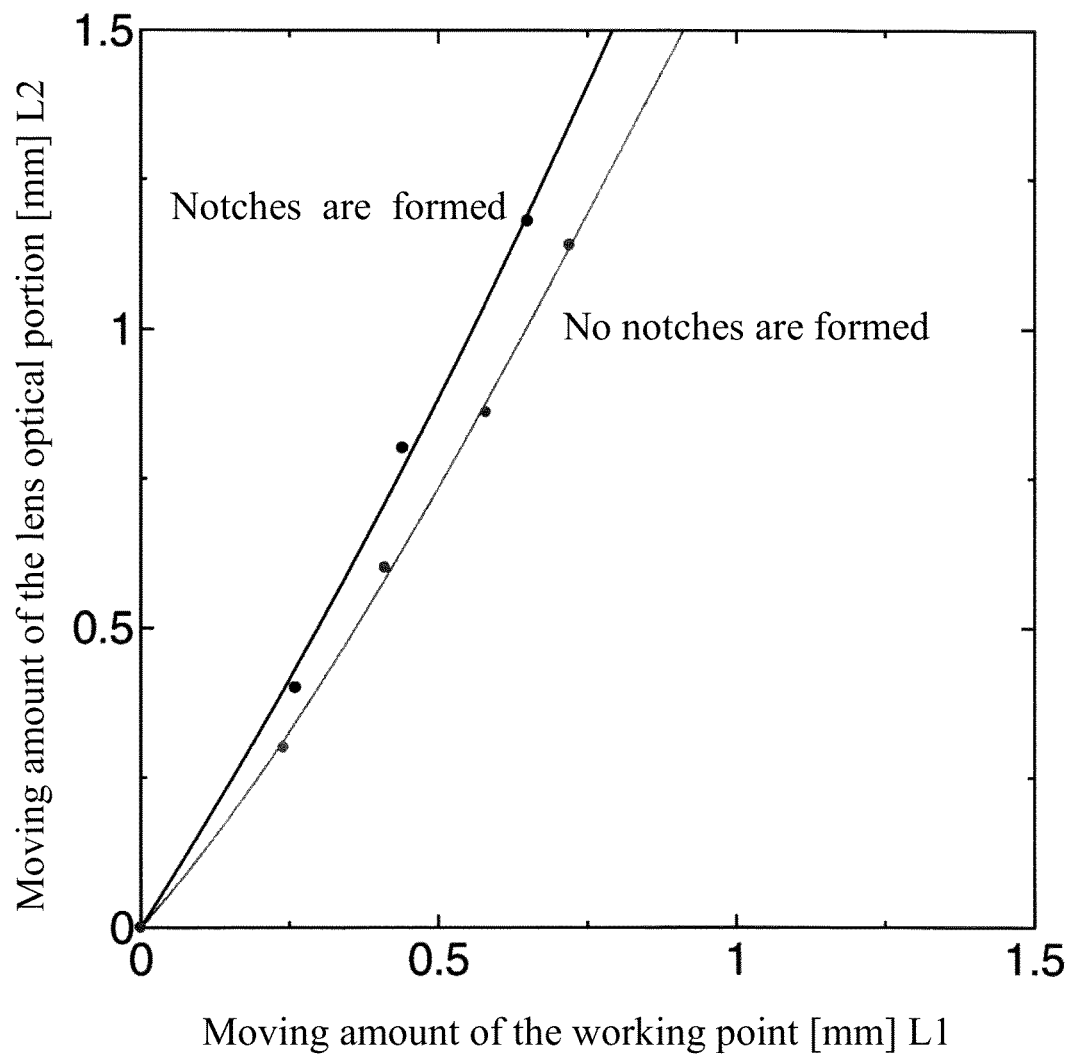
FIG. 13 is a graph showing the results of the computer simulation of FIG. 12.

As shown in FIG. 13, when the moving amount L1 of the working point contacting the anterior capsule with the anterior support portion 21 in the anterior-posterior direction and the moving amount L2 of the optical portion 10 in the anterior-posterior direction were measured, it was confirmed that the moving amount L2 of the lens optical portion was larger than the moving amount L1 of the working point, and it was confirmed that the moving amount L2 of the lens optical portion was more larger when the notches 21e were formed than when the notches 21e were not formed.

DESCRIPTION OF SYMBOLS

1: this lens
10: optical portion
20: support portion
21: anterior support portion
21a: base end portion
21b: tip end portion
21c: curved portion
21d: anterior capsule contact portion
22: posterior support portion
22a: base end portion
22b: tip end portion

The invention claimed is:

1. An accommodative intraocular lens to be installed in a lens capsule whose anterior capsule has been incised in ophthalmic surgery, the accommodative intraocular lens comprising:
   an optical portion; and
   one or a plurality of support portions arranged circumferentially around the optical portion to support the optical portion, wherein the plurality of support portions is arranged side by side at regular intervals along a circumferential direction of the optical portion,
   wherein the support portion is composed of an anterior support portion provided in a manner as to come into contact with an inner surface of an anterior capsule and a posterior support portion provided in a manner as to come into contact with an inner surface of a posterior capsule, and is configured such that the anterior support portion presses the anterior capsule and the posterior support portion presses the posterior capsule by an elastic force of the support portion,
   wherein the anterior support portion extends radially inward and forward from a base end portion connected to the posterior support portion and then extends radially inward and backward to form a curved portion, wherein the curved portion has a tip end portion at an end of the curved portion and the tip end portion contacts with a peripheral portion of the optical portion,
   wherein when the lens capsule is in a distance vision state, as a pressing force on the anterior support portion by the anterior capsule increases, the anterior support portion deflects backward while maintaining a radial position of the base end portion, so that the tip end portion of the anterior support portion moves the optical portion backward while maintaining its radial position,
   wherein when the lens capsule is in a near vision state, as the pressing force on the anterior support portion by the anterior capsule decreases, the anterior support portion returns forward by the elastic force of the support portion while maintaining the radial position of the base end portion, so that the tip end portion of the anterior support portion moves the optical portion forward while maintaining its radial position, and
   wherein the tip end portion of the anterior support portion is positioned forward of a center position of a lens capsule equatorial portion when the lens capsule is in the near vision state, while the tip end portion of the anterior support portion is positioned backward of the center position of the lens capsule equatorial portion when the lens capsule is in the distance vision state.

2. The accommodative intraocular lens as recited in claim 1,
   wherein the support portion is provided with a regulating member for maintaining the radial position of the base end portion of the anterior support portion.

3. The accommodative intraocular lens as recited claim 2, wherein the regulating member is formed in such a manner as to connect the base end portions of the anterior support portions adjacent to each other.

4. The accommodative intraocular lens as recited in claim 2, wherein the regulating member is formed in such a manner as to project radially outward at a high position of a lens capsule equatorial portion on an outer surface of the support portion.

5. The accommodative intraocular lens as recited in claim 1,
wherein the anterior support portion is provided with a longitudinally extending hole portion.

6. The accommodative intraocular lens as recited in claim 1,
wherein the anterior support portion is formed to be thinner than the posterior support portion.

7. The accommodative intraocular lens as recited in claim 1,
wherein the anterior support portion is provided with one or a plurality of circumferentially extending notches.

8. An accommodative intraocular lens to be installed in a lens capsule, the accommodative intraocular lens comprising:
an optical portion; and
one or a plurality of support portions arranged circumferentially around the optical portion to support the optical portion, the plurality of support portions is arranged side by side at regular intervals along a circumferential direction of the optical portion,
wherein the support portion is composed of an anterior support portion and a posterior support portion,
wherein the anterior support portion extends radially inward and forward from a base end portion of the anterior support portion connected to the posterior support portion and then extends radially inward and backward to form a curved portion, wherein the curved portion has a tip end portion at an end of the curved portion and the tip end portion contacts with a peripheral portion of the optical portion,
wherein when the anterior support portion deflects backward, the tip end portion of the anterior support portion is configured to be movable so as to be positioned backward of the base end portion connected to the posterior support portion and the optical portion is configured to be movable so as to be positioned backward of the base end portion accordingly,
wherein when the anterior support portion deflects forward, the tip end portion of the anterior support portion is configured to movable so as to be positioned forward of the base end portion connected to the posterior support portion and the optical portion is configured to movable so as to be positioned forward of the base end portion accordingly, and
wherein the tip end portion of the anterior support portion is positioned forward of a center position of a lens capsule equatorial portion when a lens capsule is in a near vision state, while the tip end portion of the anterior support portion is positioned backward of the center position of the lens capsule equatorial portion when the lens capsule is in a distance vision state.

9. The accommodative intraocular lens as recited in claim 8,
wherein the support portion is provided with a regulating member for maintaining a radial position of the base end portion of the anterior support portion.

10. The accommodative intraocular lens as recited claim 9,
wherein the regulating member is formed in such a manner as to connect the base end portions of the anterior support portions adjacent to each other.

11. The accommodative intraocular lens as recited in claim 8,
wherein the anterior support portion is provided with a longitudinally extending hole portion.

12. The accommodative intraocular lens as recited in claim 8,
wherein the anterior support portion is formed to be thinner than the posterior support portion.

13. The accommodative intraocular lens as recited in claim 8,
wherein the anterior support portion is provided with one or a plurality of circumferentially extending notches.

14. An accommodative intraocular lens to be installed in a lens capsule, the accommodative intraocular lens comprising:
an optical portion; and
one or a plurality of support portions arranged circumferentially around the optical portion to support the optical portion, wherein the plurality of support portions is arranged side by side at regular intervals along a circumferential direction of the optical portion,
wherein the support portion is composed of an anterior support portion and a posterior support portion, the anterior support portion has a base end portion connecting with the posterior support portion,
wherein the anterior support portion extends radially inward and forward from a base end portion of the anterior support portion connected to the posterior support portion and then extends radially inward and backward to form a curved portion, wherein the curved portion has a tip end portion at an end of the curved portion and the tip end portion contacts with a peripheral portion of the optical portion,
wherein when the anterior support portion deflects backward, the anterior support portion moves the optical portion backward while maintaining a radial position of the base end portion of the anterior support portion connected to the posterior support portion,
wherein when the anterior support portion deflects forward, the anterior support portion moves the optical portion forward while maintaining the radial position of the base end portion of the anterior support portion,
wherein a tip end portion of the anterior support portion is positioned forward of a center position of a lens capsule equatorial portion when the lens capsule is in a near vision state, while the tip end portion of the anterior support portion is positioned backward of the center position of the lens capsule equatorial portion when the lens capsule is in a distance vision state.

15. The accommodative intraocular lens as recited in claim 14,
wherein the support portion is provided with a regulating member for maintaining the radial position of the base end portion of the anterior support portion.

16. The accommodative intraocular lens as recited claim 15,
wherein the regulating member is formed in such a manner as to connect the base end portions of the anterior support portions adjacent to each other.

17. The accommodative intraocular lens as recited in claim 14,
wherein the anterior support portion is provided with a longitudinally extending hole portion.

18. The accommodative intraocular lens as recited in claim 14,
wherein the anterior support portion is formed to be thinner than the posterior support portion.

19. The accommodative intraocular lens as recited in claim 14,
wherein the anterior support portion is provided with one or a plurality of circumferentially extending notches.

* * * * *